United States Patent
Gruter et al.

(10) Patent No.: US 10,370,319 B2
(45) Date of Patent: Aug. 6, 2019

(54) PROCESS FOR THE MANUFACTURE OF AN ADIPIC ACID PRODUCT

(71) Applicant: Avantium Knowledge Centre B.V., Amsterdam (NL)

(72) Inventors: Gerardus Johannes Maria Gruter, Amsterdam (NL); Jan Cornelis Van Der Waal, Amsterdam (NL); Lisette Magnee, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

(21) Appl. No.: 15/764,195

(22) PCT Filed: Oct. 3, 2016

(86) PCT No.: PCT/NL2016/050680
§ 371 (c)(1),
(2) Date: Mar. 28, 2018

(87) PCT Pub. No.: WO2017/061858
PCT Pub. Date: Apr. 13, 2017

(65) Prior Publication Data
US 2018/0282255 A1    Oct. 4, 2018

(30) Foreign Application Priority Data
Oct. 5, 2015 (NL) ...................................... 2015557

(51) Int. Cl.
C07C 55/14 (2006.01)
C07C 51/377 (2006.01)

(52) U.S. Cl.
CPC .................................. *C07C 51/377* (2013.01)

(58) Field of Classification Search
CPC ..................................................... C07C 51/377
USPC ......................................................... 562/592
See application file for complete search history.

(56) References Cited

U.S. PATENT DOCUMENTS 8,927,768 B2 *  1/2015  Boussie ................ C07C 29/149
562/590

OTHER PUBLICATIONS

"International Search Report and Written Opinion" dated Dec. 19, 2016 from parent PCT application No. PCT/NL16/50680 filed Oct. 3, 2016.

* cited by examiner

*Primary Examiner* — Deborah D Carr
(74) *Attorney, Agent, or Firm* — Suiter Swantz pc llo

(57) ABSTRACT

Process for the manufacture of an adipic acid product by a reduction of a tetrahydrofuran dicarboxylic acid compound, wherein the tetrahydrofuran dicarboxylic acid compound is contacted with hydrogen iodide at a temperature of at least 100° C. in an inert atmosphere to yield the adipic acid product.

16 Claims, No Drawings

PROCESS FOR THE MANUFACTURE OF AN ADIPIC ACID PRODUCT

The present invention relates to a process for the manufacture of an adipic acid product, more in particular to a process for the manufacture of an adipic acid product by the reduction of a tetrahydrofuran dicarboxylic acid compound.

Such a process is known from U.S. Pat. No. 8,927,768. This patent document describes a process for preparing adipic acid from a tetrahydrofuranic substrate by contacting this substrate with hydrogen in the presence of a hydrodeoxygenation catalyst, a solvent and a halide source. The tetrahydrofuranic substrate can be tetrahydrofuran dicarboxylic acid to yield adipic acid. Halide sources that can be used are hydrogen bromide and hydrogen iodide. Examples of a hydrodeoxygenation catalyst include a noble metal, such as platinum, rhodium or palladium on a silica support.

The presence of hydrogen and a hydrodeoxygenation catalyst renders the process rather complex. Moreover, the hydrodeoxygenation catalyst may suffer from reduction of activity during the course of the reaction and owing to the strong acidity of the hydrogen halide. Such complications would be avoided if no catalyst were to be used. One could refrain from using a hydrodeoxygenation catalyst if no hydrogen would be present. However, according to U.S. Pat. No. 8,927,768 the deoxygenation only occurs in the presence of hydrogen.

It has now surprisingly been found that a tetrahydrofuranic substrate can be converted to an adipic acid product in a very good yield if the reaction is carried out in an inert atmosphere. In such an atmosphere the presence of a solid hydrodeoxygenation catalyst is not required. Accordingly, the present invention provides a process for the manufacture of an adipic acid product by a reduction of a tetrahydrofuran dicarboxylic acid compound, wherein the tetrahydrofuran dicarboxylic acid compound is contacted with hydrogen iodide at a temperature of at least 100° C. in an inert atmosphere to yield the adipic acid product.

By a reduction is herein understood a reaction wherein a compound is reduced. Such a reaction can involve one or more reactants in a reaction mixture, where at least one of the reactants is reduced. Without wishing to be bound by any kind of theory, it is believed that the reduction of a tetrahydrofuran dicarboxylic acid compound in the process of the present invention may comprise a reaction of such tetrahydrofuran dicarboxylic acid compound, wherein the tetrahydrofuran dicarboxylic acid compound is reduced.

The process according to the present invention is carried out in an inert atmosphere. For the purpose of this invention an "inert atmosphere" is understood to be an atmosphere in the substantial absence of hydrogen. Since the atmosphere substantially does not contain hydrogen, there is no need to provide for separation equipment to separate hydrogen from the rest of the reaction mixture and for the recovery of hydrogen. The absence of hydrogen simplifies the conversion of the tetrahydrofuran dicarboxylic acid compound. Further, the absence of hydrogen allows that the reaction can be carried out in the absence of a hydrodeoxygenation catalyst so that activity loss and/or selectivity loss does not occur.

In the process of the present invention a tetrahydrofuran dicarboxylic acid compound is contacted with hydrogen iodide. In this specification the term tetrahydrofuran dicarboxylic acid refers to the compound 2,5-tetrahydrofuran dicarboxylic acid. The compound may be 2,5-tetrahydrofuran dicarboxylic acid itself. However, it is also feasible to use other compounds such as an ester or a salt thereof. Also the corresponding diacyl halides, such as the chlorides, and the amides can be used as substrate in this reaction. It has been found that esters, salts and the diacid itself can most suitably be used. Therefore, the tetrahydrofuran dicarboxylic acid compound is suitably selected from the group consisting of tetrahydrofuran dicarboxylic acid, a hydrocarbyl ester of such acid, a metal salt of such acid or a combination thereof. When a hydrocarbyl ester is used, the hydrocarbyl moiety preferably has 1 to 8 carbon atoms, more preferably 1 to 4 carbon atoms, and most preferably is selected from methyl, ethyl and combinations thereof.

The second reactant in the process according to the present invention is a hydrogen iodide. The use of other hydrogen halides, such as hydrogen fluoride, hydrogen chloride or hydrogen bromide, has been found not to be effective.

The tetrahydrofuran dicarboxylic acid compound and the hydrogen iodide can be contacted as the only reactants in the reaction mixture. However, since the tetrahydrofuran dicarboxylic acid compounds tend to be solid and the hydrogen iodide is gaseous, the contact between these reactants may be suboptimal if they are used in a solid and gaseous form, respectively. It would be advantageous to conduct the reaction in a liquid phase. An option is to operate above the melting temperature of the tetrahydrofuran dicarboxylic acid compounds and at a sufficiently high pressure to obtain dissolution of the hydrogen iodide in the melt. However, the use of a solvent would render the operation easier.

Therefore, the reaction is preferably carried out in the presence of a solvent. The solvent provides for a homogeneous distribution of the reactants. It further provides an elegant medium for the heat transfer that is desired in the present reaction. Since the solvents do not have to dissolve hydrogen, as is the case in the process according to U.S. Pat. No. 8,927,768, the solvents may be selected from a wide range of possible liquids. Suitable solvents include water and carboxylic acids, amides, esters, lactones, sulfoxides, sulfones and mixtures thereof. Preferred solvents include water, weak carboxylic acids and mixtures of water and one or more weak carboxylic acids. The weak carboxylic acid suitably has a pKa at 25° C. of at least 3, preferably in the range of 3 to 6. A preferred weak carboxylic acid comprises from 1 to 4 carbon atoms, and may be selected from formic acid, acetic acid, propionic acid, butyric acid and mixtures thereof. The most preferred acid is acetic acid.

It has been found that mixtures of water and a weak carboxylic acid are especially suitable. Although in a pure carboxylic acid, such as glacial acetic acid, the reaction can conveniently be carried out and results in satisfactory yields, it has emerged that when a certain amount of water is added to the acid, the yield increases. When too much water is added the yield decreases again. Therefore, the solvent preferably comprises water, and more preferably, the amount of water is in the range of 0.2 to 30 vol %, based on the volume of the solvent. The tetrahydrofuran dicarboxylic acid compound may be present in the solvent in a wide range of concentrations. It has been found very suitable that the concentration of the tetrahydrofuran dicarboxylic acid compound in the solvent is in the range of 10 to 500 g/l, preferably from 25 to 250 g/l. Water may be added as a separate component for the solvent. However, it is very convenient to add hydrogen iodide as an aqueous solution. By using a convenient concentration of hydrogen iodide in water it is practically easy to ensure that the desired amount of hydrogen iodide and the desired amount of water is added to the reaction mixture. The contact between the tetrahydrofuran dicarboxylic acid compound and hydrogen iodide may conveniently be conducted in the presence of just the aqueous solution of hydrogen iodide.

The reaction results in an adipic acid product in good yield. Without wishing to be bound by any theory, it is believed that the hydrogen iodide achieves the substitution with an iodide radical at the 2- and 5-position of the furan ring and the release of a water molecule with the oxygen atom of the furan ring to establish ring opening. The result may be a 2,5-disubstitued adipic acid product, wherein the substituents are selected from hydroxyl groups and iodide moieties. Under the influence of other hydrogen iodide molecules the substituents are replaced by hydrogen and the iodine atoms obtained thereby combine with the iodine from the hydrogen iodide to form an iodine molecule and an adipic acid product.

It is surprising that this reaction mechanism occurs since the tetrahydrofuran dicarboxylic acid compound only has two moderately strong electron-withdrawing groups, i.e. the carboxylic groups. These electron-withdrawing groups have limited influence on the capability of accomplishing not only the substitution by iodine, but also the release of the oxygen atom of the furan ring to form water. This is the more surprising now that the reaction is not conducted in a reducing atmosphere and the presence of a hydrodeoxygenation catalyst is not required. It is further apparent that the reaction mechanism of the reaction of the present invention differs from that of the process of U.S. Pat. No. 8,927,768; whereas hydrogen bromide appears to work in the presence of hydrogen and a hydrodeoxygenation catalyst, such is not the case in the absence of hydrogen and a hydrodeoxygenation catalyst.

The inert atmosphere does not need to be a gaseous atmosphere. As indicated above, the inert atmosphere is substantially free from hydrogen. The atmosphere may comprise a gaseous phase, but it is also possible to work in an all-liquid environment. Due to the absence of hydrogen there is no need to involve the use of a hydrodeoxygenation catalyst. Therefore, the process according to the present invention is preferably carried out in the absence of a hydrodeoxygenation catalyst.

Suitably, the atmosphere is also substantially free from any oxygen. It is therefore not preferred to conduct the reaction in air. When the inert atmosphere comprises a gas, the inert atmosphere preferably comprises a gas selected from the group consisting of nitrogen, noble gases, carbon dioxide, steam and combinations thereof. More preferably, the inert atmosphere consists of these gases or their combinations. By noble gases are understood the gases of group 18 of the Periodic Table of the Elements. The most suitable noble gases are helium, neon and argon. These gases may be present in combination with other inert gases, if desired. The inert atmosphere may also be formed by the vapor pressure of the reaction mixture. This is the more relevant when the reaction is conducted in the presence of a solvent. The inert atmosphere may then comprise the vapor from the solvent. The present invention has the advantage that it can be conducted in reactors that only contain liquids. In such a case a gas space or gas cap does not need to be present. The inert atmosphere consists of the reaction medium itself. The inert atmosphere may thus suitably comprise a gas selected from the group consisting of nitrogen, noble gases, carbon dioxide, steam and combinations thereof or consist of liquids. Such liquids suitably comprise the tetrahydrofuran dicarboxylic acid compound, hydrogen iodide and optionally reaction products thereof and/or a solvent.

The process according to the invention may be carried out in a batch, semi-batch or continuous mode. Advantageously, the process is conducted in a continuous mode. Suitable reactors are, trickle flow reactors or continuous stirred tank reactors, which can be operated in a simple fashion. When the process is conducted in the absence of a gaseous reactant, plug flow reactors are also very convenient.

As indicated above, according to a suggested reaction mechanism the hydrogen iodide may react with the tetrahydrofuran dicarboxylic acid compound whilst forming a iodine molecule and an adipic acid product. The stoichiometric ratio between hydrogen iodide and the tetrahydrofuran dicarboxylic acid compound would thus preferably be 4:1. Accordingly, the process of the present invention is suitably carried out with a molar ratio of hydrogen iodide to the tetrahydrofuran dicarboxylic acid compound of equal to or more than about 4. Typically, the molar ratio of the hydrogen iodide to the tetrahydrofuran dicarboxylic acid compound is in the range of 4:1 to 25:1, more preferably, from 5:1 to 10:1, and most preferably in the range of from 5.5:1 to 6.5:1, such as 6:1.

The temperature at which the process according to the present invention can be carried out may vary within wide ranges. The reaction temperature may be as low as ambient temperature, i.e. 20° C. However, at this temperature the reaction rate is very slow. Therefore, the reaction is suitably carried out at elevated temperature, e.g. at least 100° C., preferably at least 120° C. Advantageously, the tetrahydrofuran dicarboxylic acid compound is contacted with hydrogen iodide at a temperature in the range of 130 to 300° C., preferably, from 140 to 250° C., most preferably from 150 to 200° C.

The reaction pressure can also be selected from a wide range. Since there is no need to dissolve any hydrogen into the reaction mixture, as is the case in the process according to U.S. Pat. No. 8,927,768, the reaction pressure is not critical. Since it is advantageous to conduct the reaction in the liquid phase the pressure is suitably selected such that the reaction mixture is liquid, e.g. in view of the reaction temperature that is being applied. Typically, the tetrahydrofuran dicarboxylic acid compound is contacted with hydrogen iodide at a pressure of 2 to 100 bar, preferably from 5 to 75 bar, more preferably from 10 to 60 bar.

The duration of the contact between the tetrahydrofuran dicarboxylic acid compound and hydrogen iodide may vary. It has been found that hardly any degradation products of the adipic acid product are obtained in the reaction. The contact may therefore be prolonged at the conditions and for a period as desired to arrive at the most effective and efficient yield of adipic acid product. Typically it has been found that the contact is conducted for a period in the range of 0.25 to 25 hours. Dependent on the reaction conditions, in particular on the temperature the reaction period may be optimized. Very good results are obtainable when the tetrahydrofuran dicarboxylic acid compound is contacted with the hydrogen iodide for a period in the range of 0.5 to 10 hours.

After contacting the tetrahydrofuran dicarboxylic acid compound with hydrogen iodide a product mixture is obtained that comprises the adipic acid product, iodine molecules and optionally unreacted hydrogen iodide. The adipic acid product is suitably separated from the product mixture. Preferably, this is done after the separation of iodine and hydrogen iodide from the reaction product. The iodine and hydrogen iodide can conveniently be removed from the product mixture by the use of an ion exchange resin. The resulting mixture of adipic acid product and solvent is suitably divided into the adipic acid product and the solvent by means of distillation. The iodine obtained may be recovered as a separate product of the present process. The absence of the heterogeneous catalyst as employed in the process according to U.S. Pat. No. 8,927,768 is very beneficial in facilitating the recovery process.

A number of processes are known for recovering iodine, such as, for example, the adsorption process which employs activated carbon, silver charged activated carbon or other, preferably silver charged sorbents such as silica. Other processes for collecting iodine employ ion exchangers, or introduce precipitation or co-precipitation. Another process uses liquid/liquid extraction. Most of these processes cover only certain chemical forms of iodine, such as, for example, the process in which there is a fixation of iodide at silver chloride. Or copper chloride. According to the process of U.S. Pat. No. 4,461,711 the separation and collection of iodine takes place by filtration through activated carbon. The activated carbon can be an activated carbon which is impregnated with silver or can be a non-impregnated activated carbon. The iodine that is absorbed may be recovered as product. Alternatively, the absorbed iodine may be reduced to iodide, in particular to hydrogen iodide. The hydrogen iodide may conveniently be recycled to be contacted with the tetrahydrofuran dicarboxylic acid compound.

The starting compound of the present process, i.e. tetrahydrofuran dicarboxylic acid compound, may suitably be obtained from the corresponding furandicarboxylic acid compound by hydrogenation thereof. The present invention thus provides also a process for the preparation of an adipic acid product comprising: hydrogenating a furandicarboxylic acid compound to obtain a tetrahydrofuran dicarboxylic acid compound; and contacting the tetrahydrofuran dicarboxylic acid compound with hydrogen iodide in an inert atmosphere to yield the adipic acid product. A suitable method for this hydrogenation has been described in U.S. Pat. No. 8,927,768. Reaction conditions that are suitable for this conversion include the use of a hydrogenation catalyst. As indicated in U.S. Pat. No. 8,927,768 suitable hydrogenation catalysts include heterogeneous catalysts, including solid-phase catalysts comprising one or more supported or unsupported metals. Preferably, the metal is or the metals are present on the surface of a support. Suitably the metal or metals is/are selected from the group consisting of palladium, platinum, rhodium, ruthenium, nickel, cobalt, iron and combinations thereof. Additional other metals may be present, including one or more transition metals, alone or in combination with one or more rare earth metals (e.g. lanthanides), alone or in combination with one or more main group metals (e.g. Al, Ga, Tl, In, Sn, Pb or Bi). In general, the metals may be present in various forms (e.g., elemental, metal oxide, metal hydroxides, metal ions, etc.). Typically, the metal or metals on the surface of a support may constitute from about 0.25% wt to about 10% wt, suitably from 1% wt to 8% wt, more preferably from 2.5% wt to 7.5% wt (e.g., 5% wt) of the total weight of the catalyst.

Suitable catalyst supports include carbon, alumina, silica, silica-alumina, ceria, titania, zirconia, niobia, magnesia, clays, iron oxide, silicon carbide, crystalline aluminosilicates, zeolites, and combinations thereof. The support materials may be modified using methods known in the art such as heat treatment, acid treatment or by the introduction of a dopant. Examples include metal-doped titanias, metal-doped zirconias, e.g., tungstated-zirconia, metal-doped cerias, and metal-modified niobias. Particularly preferred supports are carbon, which may be activated carbon, carbon black, coke or charcoal, alumina, zirconia, titania, zeolites, silica or a combination of one or more thereof. Most preferably, the support of the hydrogenation catalyst is selected from the group consisting of carbon, zirconia, zeolites, and silica and combinations thereof.

Generally, the temperature of the hydrogenation reaction is at least 30° C., more typically 60° C., or higher. Suitably, the temperature of the hydrogenation reaction is in the range of 60° C. to 200° C., and more preferably in the range of 60° C. to 160° C.

Typically, the partial pressure of hydrogen in the hydrogenation reaction is at least 2 bar, preferably at least 5 bar. The hydrogen partial pressure may be as high as 100 bar, although such high pressures are typically not required. Suitably the hydrogen partial pressure is in the range of 5 to 100 bar, more preferably from 15 to 60 bar.

Suitable furandicarboxylic acid compounds that can be used to obtain the corresponding tetrahydrofuran dicarboxylic acid compound include furandicarboxylic acid, esters thereof, amides thereof and/or halides thereof. Preferably 2,5-furandicarboxylic acid is used as starting material for the hydrogenation to obtain the tetrahydrofuran dicarboxylic acid compound. The tetrahydrofuran dicarboxylic acid compound that is used in the process of the present invention has therefore suitably been obtained from the hydrogenation of a 2,5-furandicarboxylic acid compound wherein the hydrogenation has been carried out with a hydrogen-containing gas in the presence of a hydrogenation catalyst.

2,5-Furandicarboxylic acid or esters thereof can be obtained from biomass. In WO2007/104514 and WO2007/104515 methods have been described wherein carbohydrate-containing biomass is converted into ethers or esters of 5-hydroxymethyl furfural (5-HMF). 5-HMF itself and ethers and esters thereof can further be oxidized to furandicarboxylic acid or an ester thereof as described in e.g. U.S. Pat. No. 8,519,167 and U.S. Pat. No. 8,865,921.

The 2,5-furandicarboxylic acid is thus suitably obtained from the oxidation of 5-HMF or an ether or ester thereof. In accordance with the teachings of U.S. Pat. No. 8,519,167 and U.S. Pat. No. 8,865,921 the oxidation catalyst may be a homogeneous or heterogeneous catalyst. Suitably the catalyst is a homogeneous catalyst comprising cobalt and manganese, and optionally, bromine. Since the furandicarboxylic acid compound can conveniently be obtained from the dehydration of biomass, the present invention also provides a process for the preparation of an adipic acid product wherein a carbohydrate-containing biomass starting material is converted in the presence of an acid catalyst to a 5-hydroxymethyl furfural compound, wherein the 5-hydroxymethylfurfural compound is oxidized to a furandicarboxylic acid compound, wherein the furandicarboxylic acid compound is hydrogenated to obtain a tetrahydrofuran dicarboxylic acid compound, and the tetrahydrofuran dicarboxylic acid compound is contacted with a hydrogen iodide in an inert atmosphere, preferably at a temperature of at least 100° C., in accordance with the above-described process to obtain the adipic acid product. This process has several advantages. The oxidation of the 5-hydroxymethylfurfural compound to a furandicarboxylic acid compound can be achieved in a solvent of acetic acid. The same solvent can be used in the subsequent hydrogenation of the furandicarboxylic acid compound to the tetrahydrofuran dicarboxylic acid compound. The reduction of the tetrahydrofuran dicarboxylic acid compound by contacting it with a hydrogen iodide can also take place in acetic acid. Therefore, the complete reaction route from 5-HMF compound to adipic acid product may be accomplished in the same solvent.

The process will be further illustrated by means of the following examples.

EXAMPLE 1

2,5-Furan dicarboxylic acid (FDCA) (64.4 mg) and a hydrogenation catalyst comprising 5% wt palladium on carbon (9.4 mg) were mixed with 900 μL of glacial acetic acid. The reaction mixture was put under a hydrogen pressure of 50 bar and heated to 140° C. for 190 minutes. Hydrogen was then replaced by nitrogen, the reaction mixture was cooled and analyzed. The analysis showed that the FDCA was quantitatively converted into tetrahydrofuran dicarboxylic acid (THFDCA).

EXAMPLE 2

In a series of experiments tetrahydrofuran-2,5-dicarboxylic acid (THFDCA) was weighed and mixed with an amount of an aqueous solution of hydrogen iodide (57% wt HI). The reactor volume was filled to 1 ml by addition of glacial acetic acid. A pressure of 50 bar nitrogen was applied and the reaction mixture was allowed to react for a particular period at various temperatures. After the reaction period the reaction mixture was cooled and analyzed. Only adipic acid was detected as product. In some cases some unreacted tetrahydrofuran dicarboxylic acid was found. In the Table the yields of each acid, based on the sum of both acids, have been given.

The reaction conditions and results are shown in Table 1 below.

TABLE 1

| Exp. No. | THFDCA mmol | HI, mmol | HI/THFDCA mol/mol | solution HI, μl | AcOH μl | T, ° C. | duration min. | Yield adipic acid, % | Yield THFDCA, % |
|---|---|---|---|---|---|---|---|---|---|
| 1 | 0.291 | 0.589 | 2.0 | 77 | 923 | 160 | 250 | 55.5 | 44.5 |
| 2 | 0.294 | 1.766 | 6.0 | 230 | 770 | 160 | 250 | 100.0 | 0.0 |
| 3 | 0.293 | 2.944 | 10.0 | 385 | 615 | 160 | 250 | 100.0 | 0.0 |
| 4 | 0.294 | 1.169 | 4.0 | 154 | 846 | 160 | 70 | 48.3 | 51.7 |
| 5 | 0.290 | 1.754 | 6.0 | 230 | 770 | 160 | 70 | 91.2 | 8.8 |
| 6 | 0.294 | 1.754 | 6.0 | 230 | 770 | 180 | 70 | 100.0 | 0.0 |

The results show that at a molar ratio of HI/THFDCA of about 6.0 very good yields are obtainable. At reaction temperatures of 160 and 180° C. a virtually quantitative yield is attainable. The reaction duration may be varied to obtain a quantitative yield whilst no by-products are formed.

EXAMPLE 3

Similar experiments as those described for Example 2 were conducted. In one experiment no solvent was used. The reaction temperature was 140° C. and the duration of the experiments was 310 min.

The results are shown in Table 2.

TABLE 2

| Exp. No. | THFDCA mmol | HI, mmol | HI/THFDCA mol/mol | solution HI, μl | AcOH μl | T, ° C. | duration min. | Yield adipic acid, % | Yield THFDCA, % |
|---|---|---|---|---|---|---|---|---|---|
| 7 | 0.630 | 1.169 | 4.0 | 154 | 846 | 140 | 310 | 10.4 | 89.6 |
| 8 | 0.633 | 1.169 | 4.0 | 154 | — | 140 | 310 | 16.7 | 83.3 |

Comparison between the results of Experiment Nos. 7 and 8 shows that when the reaction is conducted in water only, the yield, which is expected to be very low, is enhanced, compared to the reaction conducted in the presence of additional acetic acid.

EXAMPLE 4

To show the influence of the solvent some experiments were conducted with an additional amount of water. The procedure was as described for the experiments of Example 2. The reaction conditions included a reaction temperature of 160° C. and a reaction duration of 250 minutes. Other reaction conditions and results are shown in Table 3.

TABLE 3

| Exp. No. | THFDCA mmol | HI, mmol | HI/THFDCA mol/mol | HI solution, µl | AcOH µl | water in HI solution, µl | Extra water, µl | Yield adipic acid, % | Yield THFDCA, % |
|---|---|---|---|---|---|---|---|---|---|
| 1 | 0.291 | 0.589 | 2.0 | 77 | 923 | 62 | — | 55.5 | 44.5 |
| 9 | 0.292 | 0.589 | 2.0 | 77 | 873 | 62 | 50 | 48.3 | 51.7 |
| 10 | 0.292 | 0.589 | 2.0 | 77 | 673 | 62 | 250 | 25.4 | 74.6 |

The experiments show that very good adipic acid yields are obtained when the amount of water is in the range of about 5 to 30 vol %, based on the solvent, i.e. the sum of acetic acid and water. It is observed that also for Experiment Nos. 9 and 10 the yield of adipic acid is expected to be increased if the ratio of HI/THFDCA is increased.

EXAMPLE 5

To show that HBr acts differently from HI in the absence of hydrogen four experiments were conducted. In these experiments tetrahydrofuran dicarboxylic acid (THFDCA) was weighed and mixed with an amount of an aqueous solution of hydrogen iodide (57% wt HI) or an aqueous solution of hydrogen bromide (48 wt % HBr). To the reactor glacial acetic acid was added. Additionally, a catalytic amount of a palladium-on-carbon hydrogenation catalyst (5% Pd/C) was added. In two experiments a pressure of 50 bar of nitrogen was applied. In the two other experiments a pressure of 50 bar of hydrogen was applied. The reaction mixture was allowed to react for a particular period at 160° C. After the reaction period the reaction mixture was cooled and analyzed. The Table 4 shows the actual yields isolated for adipic acid and THFDCA. The results are shown in Table 4 below.

TABLE 4

| Exp No. | THFDCA mmol | HI or HBr, solution, µl | AcOH µl | Pd/C, mg | Gas | Duration, min | Yield adipic acid, % | Yield THFDCA, % |
|---|---|---|---|---|---|---|---|---|
| 11 | 0.268 | HI, 41 | 959 | 8.4 | $H_2$ | 193 | 88.2 | 0.0 |
| 12 | 0.297 | HBr, 51 | 949 | 9.3 | $H_2$ | 195 | 68.9 | 0.0 |
| 13 | 0.298 | HI, 231 | 769 | 9.4 | $N_2$ | 250 | 98.7 | 0.0 |
| 14 | 0.298 | HBr, 204 | 937 | 9.5 | $N_2$ | 192 | 0.0 | 24.8 |

The results show that in the experiments with HBr and $H_2$ a complete conversion of THFDCA is obtained, just as in the case of HI and $H_2$. When no hydrogen is present a partial conversion of THFDCA takes place in the presence of HBr and no adipic acid is formed. Further analysis of the reaction mixture showed the presence of brominated compounds, which were not converted to adipic acid by HBr. To the extent that iodated compounds are formed in the reaction with HI, such compounds are converted to adipic acid, as shown in Experiment No. 13.

The invention claimed is:

1. A method for the manufacture of an adipic acid product by a reduction of a tetrahydrofuran dicarboxylic acid compound, wherein the tetrahydrofuran dicarboxylic acid compound is tetrahydrofuran dicarboxylic acid, a hydrocarbyl ester of such acid, a metal salt of such acid or a combination thereof, wherein the tetrahydrofuran dicarboxylic acid compound is contacted with hydrogen iodide at a temperature of at least 100° C. in an inert atmosphere to yield the adipic acid product.

2. A method according to claim 1, which is carried out in the presence of a solvent.

3. A method according to claim 2, wherein the solvent is acetic acid, acetic anhydride or a mixture thereof.

4. A method according to claim 2, wherein the solvent comprises water.

5. A method according to claim 4, wherein an amount of water is in a range of 0.2 to 30 vol %, based on a volume of the solvent.

6. A method according to claim 2, wherein a concentration of the tetrahydrofuran dicarboxylic acid compound in the solvent is in a range of 10 to 500 g/l.

7. A method according to claim 1, which is carried out in the absence of a hydrodeoxygenation catalyst.

8. A method according to claim 1, wherein the inert atmosphere comprises a gas selected from the group consisting of nitrogen, noble gases, carbon dioxide, steam and combinations thereof.

9. A method according to claim 1, which is carried out in a continuous mode.

10. A method according to claim 1, wherein a molar ratio of hydrogen iodide to tetrahydrofuran dicarboxylic acid compound is in a range of 4:1 to 25:1.

11. A method according to claim 1, wherein the tetrahydrofuran dicarboxylic acid compound is contacted with hydrogen iodide at a temperature in the range of 130 to 300° C.

12. A method according to claim 1, wherein the tetrahydrofuran dicarboxylic acid compound is contacted with the hydrogen iodide at a pressure of 2 to 100 bar.

13. A method according to claim 1, wherein the tetrahydrofuran dicarboxylic acid compound is contacted with the hydrogen iodide for a period in a range of 0.5 to 10 hours.

14. A method according to claim 1, wherein the tetrahydrofuran dicarboxylic acid compound has been obtained from the hydrogenation of furan dicarboxylic acid.

15. A method according to claim 14, wherein the hydrogenation of furan dicarboxylic acid has been carried out with a hydrogen-containing gas in the presence of a hydrogenation catalyst.

16. A method for the preparation of an adipic acid product, wherein a carbohydrate-containing biomass starting material is converted in the presence of an acid catalyst to a 5-hydroxymethyl furfural compound, wherein the 5-hydroxymethyl furfural compound is oxidized to a furandicarboxylic acid compound,
- wherein the furandicarboxylic acid compound is hydrogenated to obtain a tetrahydrofuran dicarboxylic acid compound, wherein the tetrahydrofuran dicarboxylic acid compound is tetrahydrofuran dicarboxylic acid, a hydrocarbyl ester of such acid, a metal salt of such acid or a combination thereof; and
- wherein the tetrahydrofuran dicarboxylic acid compound is contacted with a hydrogen iodide in an inert atmosphere, at a temperature of at least 100° C., to obtain the adipic acid product.

* * * * *